(12) United States Patent
Yon et al.

(10) Patent No.: US 10,004,921 B2
(45) Date of Patent: Jun. 26, 2018

(54) DEVICE FOR THERAPEUTIC TREATMENT AND METHOD FOR CONTROLLING A TREATMENT DEVICE

(71) Applicant: Theraclion SA, Malakoff (FR)

(72) Inventors: Sylvain Yon, Bagneux (FR); Francois Lacoste, Gentilly (FR)

(73) Assignee: Theraclion, Malakoff (FR)

(*) Notice: Subject to any disclaimer, the term of this patent is extended or adjusted under 35 U.S.C. 154(b) by 0 days. days.

(21) Appl. No.: 14/383,513

(22) PCT Filed: Mar. 14, 2013

(86) PCT No.: PCT/EP2013/055209
§ 371 (c)(1),
(2) Date: Sep. 5, 2014

(87) PCT Pub. No.: WO2013/135801
PCT Pub. Date: Sep. 19, 2013

(65) Prior Publication Data
US 2015/0088039 A1 Mar. 26, 2015

(30) Foreign Application Priority Data

Mar. 14, 2012 (EP) .................................... 12159445

(51) Int. Cl.
A61H 1/00 (2006.01)
A61N 7/02 (2006.01)
(Continued)

(52) U.S. Cl.
CPC ...... A61N 7/02 (2013.01); A61B 2018/00845 (2013.01); A61B 2018/00886 (2013.01); A61B 2090/378 (2016.02)

(58) Field of Classification Search
CPC .................................... A61N 7/02; A61N 7/00
(Continued)

(56) References Cited

U.S. PATENT DOCUMENTS

2007/0106157 A1* 5/2007 Kaczkowski .......... A61B 5/015
600/438
2011/0319793 A1* 12/2011 Hynynen ................. A61N 7/02
601/2
(Continued)

FOREIGN PATENT DOCUMENTS

EP 1990010 11/2008
EP 2559375 A1 2/2013
WO 2010/020730 2/2010

OTHER PUBLICATIONS

Zheng, "Targeting Method Based on Acoustic Backscatter for Treatment Planning in Tissue Ablation Using Focused Ultrasound", XP-002680759, IEEE Transactions on Biomedical Engineering, vol. 57, No. 1, Jan. 2010
(Continued)

Primary Examiner — Hien Nguyen
(74) Attorney, Agent, or Firm — Davis & Bujold PLLC; Michael J. Bujold

(57) ABSTRACT

A device (1) and a method for therapeutic treatment comprising an acoustic treatment transducer (2) able to emit high intensity waves (HIFU) toward a target (3) in order to treat the target. The high intensity waves have a focal point. The device com-prises at least one detector (15) for detecting a change of tis-sue properties caused by the high intensity waves in the target (3). The device (1) further comprises at least one means for time measurement able to measure the time $t_{mark}$ from the beginning of the emission of a pulse of HIFU until a change of tissue properties is detected or means for detecting the frequency of appearance of changes of tissue properties.

12 Claims, 8 Drawing Sheets

Figure 1:
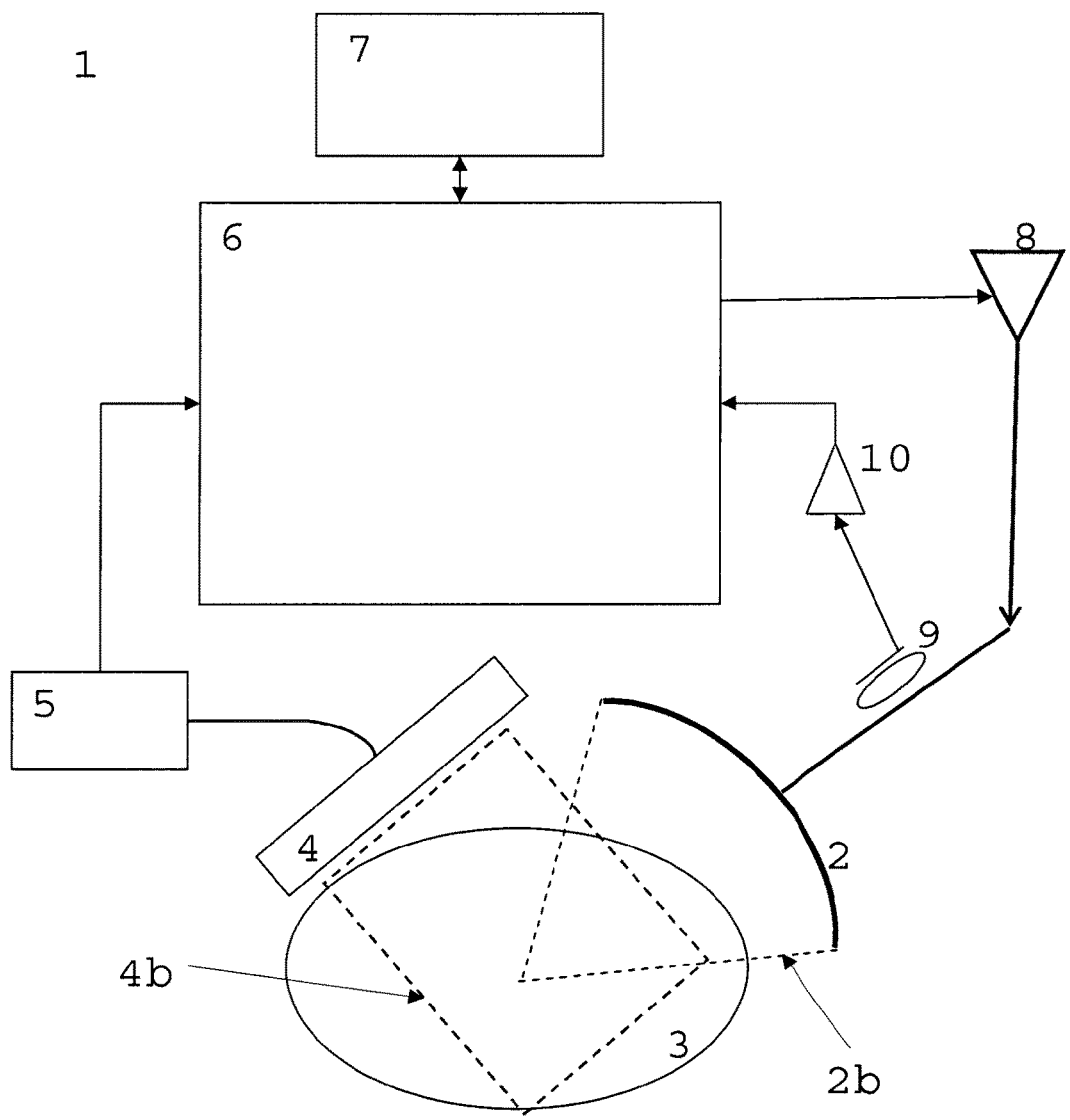

(51) Int. Cl.
*A61B 18/00* (2006.01)
*A61B 90/00* (2016.01)

(58) Field of Classification Search
USPC .............................................................. 601/3
See application file for complete search history.

(56) References Cited

U.S. PATENT DOCUMENTS

2012/0289827 A1* 11/2012 Ismail ...................... A61B 5/05
  600/430
2013/0046178 A1 2/2013 Cho et al.

OTHER PUBLICATIONS

Simon et al., Two-Dimensional Temperature Estimation Using Diagnostic Ultrasound, IEEE Transactions on Ultrasonics, Ferroelectrics, and Frequency Control, Jul. 1998, pp. 1088-1099, vol. 45, No. 4.
European Office Action issued in corresponding European Patent Application No. 13 709 120.3 dated Mar. 16, 2016.

* cited by examiner

DEVICE FOR THERAPEUTIC TREATMENT AND METHOD FOR CONTROLLING A TREATMENT DEVICE

The present invention relates to a device for therapeutic treatment and a method for controlling a therapeutic treatment device according to the independent claims.

In particular the invention concerns treatments by focused high intensity ultrasounds (HIFU).

Conventionally, in the HIFU (High intensity focused ultrasound) technology, an acoustic treatment transducer emits concentrated acoustic waves into a target tissue. These waves are absorbed by the tissue, which provokes a temperature rise in the tissue in the focal region. This temperature elevation in turn allows the creation of a necrosis and thereby allows destruction of living tissue at a distance without any direct contact.

One of the main challenges associated with the HIFU technique is the control of the temperature increase and of the size of the lesion created with this technique. Among the possibilities for control some device implement MRI imaging which allows a direct visualisation of the temperature in the treated area. Those MRI systems are however expensive and lead to high costs of treatment.

Furthermore, indirect measurements using ultrasound imaging as an indication of temperature or lesion size have been proposed e.g. in WO 2010/020730.

Some HIFU systems that are guided by ultrasound use constant intensity values to obtain a correct treatment efficacy. Such an approach is only possible when the target to be treated is very close to the HIFU source. In cases when the HIFU beam has to go through skin and potentially other layers of tissue before reaching the targeted area the use of constant values to adapt the treatment efficacy would not allow to compensate for the different configurations of the ultrasound path which would lead to very large variations of the acoustical intensities in the targeted area.

Another approach is to use the occurrence of hyperechoic marks (HEM) as an indicator for the local changes of tissue properties. Such an approach has for example been described in WO 2010/020730 or WO 2011/036485. Due to the fact that the detection of the apparition of hyperechoic marks is not easy and hyperechoic marks occur in a temperature range of approximately 80° C. to 100° C., the detection of hyperechoic marks is not considered sufficiently reliable for the control of HIFU treatments.

It is an object of the present invention to prevent the disadvantages of the prior art and in particular to create a device and a method that create a reliable way to control the effect of the treatment on the target.

The object is achieved by a device and a method according to the independent claims.

In particular, the object is achieved by a device for therapeutic treatment comprising at least an acoustic treatment transducer, at least one detector and at least one means for time measurement or means for detecting the frequency of appearance of changes of tissue properties. The acoustic treatment transducer is able to emit high intensity waves (HIFU) toward a target in order to treat the target, wherein the high intensity waves have a focal point. The detector is able to detect a change of tissue properties caused by the high intensity waves at the target in a manner basically known to the skilled person. The means for time measurement is able to measure the time $t_{mark}$ from the beginning of emission of a pulse of HIFU until changes of tissue properties are detected.

In the present context changes of tissue properties are defined to be any sign of a change in the acoustic properties of tissue under treatment. In particular, the invention refers to observations of changes of tissue per se. In particular, the change in the properties of the tissue without any changes of the environment within the tissue is observed, in particular, e.g. without the presence of any additional agents such as contrast agents. Preferably, the changes in acoustic properties are hyperechoic marks. The change in the acoustic properties of the tissue can be broadband emissions, which can occur due to cavitation. In particular hyperechoic marks are a manifestation of increased acoustic reflectivity of the tissue in the treated area, notably originating from newly created gas bubbles. Furthermore, such changes can for example stem from temperature increase and tissue boiling, inertial cavitation or tissue hardening. In particular, the temperature increase and tissue boiling caused thereby can be considered as a phase change of the tissue per se which can be observed in accordance with the present invention. Hyperechoic marks may reflect the sudden occurrences of bubbles in the tissue, which will locally increase the reflection of incoming ultrasonic waves back to the transducer. Those reflected waves may in turn be detected by whitening on the ultrasonic image of the treated area or by a surge in the reflected electrical signal to the HIFU transducer.

The device allows for an indirect control of the HIFU treatment by means of measuring a time which consequently leads to a reliable but nevertheless cost efficient device.

Based on the measured value of $t_{mark}$, the power $P_e$ and/or the pulse duration $t_{on}$ of the HIFU transducer is adapted to obtain an optimal treatment result.

It is observed in real treatment situations that $t_{Mark}$ values may vary from one pulse to the other. Since HIFU pulses are also limited in time (typically a few seconds), this leads to situations where changes in tissue properties do only appear for some pulses. An example of such a situation is a case where $t_{on}=4$ s, while the median value of $t_{Mark}$ is 3 s and $t_{Mark}$ Interquartile Range (IQR) is 2 s. In such a situation, only ¾ of the pulses will exhibit changes of tissue properties. For this reason, the rate of apparition of changes of tissue properties can also be taken into account for the control of HIFU treatment.

According to the invention $P_e$ represents either a constant value of electrical power for the duration of the pulse, or a variable power law $P_e(t)$ which by definition is not null over the pulse duration $t_{on}$.

The detector can comprise a acoustic imaging transducer, preferably a second acoustic imaging transducer, able to emit waves to provide an imaged representation of the target and of its environment.

The imaged representation of the target can be provided before, during, or after the emission of the power waves from the high intensity transducer. By means of such a device the HIFU impact at the target can be controlled in a cost-effective way.

The focal point of the emitted HIFU waves can be in an ultrasound imaging plane of the second acoustic imaging transducer.

By such an arrangement the imaging transducer enables to detect the occurrence of changes of tissue properties directly at the target without any delay.

The detector can comprise a device for detection of variation of pattern of interference during HIFU pulse as for example described in WO 2010/020730.

The device detects changes of tissue properties, in particular hyperechoic marks, by means of the detection of a change of structure of the interference image, wherein the interference image is created due to an interference of the HIFU transducer waves with the imaging transducer waves.

The use of the variation of pattern of interference during HIFU pulse enables uninterrupted firings of the HIFU transducer. This leads to a more efficient treatment.

According to another aspect of the invention, there is provided a device for therapeutic treatment, preferably as described above, comprising an acoustic treatment transducer a radio frequency generator generating a radiofrequency signal to power the acoustic treatment transducer and a detector. The detector includes a radiofrequency directional coupler able to detect the characteristic features of the reflected radiofrequency signal. The radiofrequency coupler is arranged on the power line of the HIFU transducer, which will allow the separation between the forward radiofrequency power (used for therapeutic ultrasound generation by the transducer) and its reflected part.

The characteristics features of interest in the reflected signal may be its envelope, or its spectral content along with their respective evolution with time or other characteristic features of a radiofrequency signal. A change in the reflected part of the radiofrequency signal is indicative of a local change of the tissue properties so that a monitoring of the reflected part of the radiofrequency signal is equivalent to monitoring changes of tissue properties, in particular hyperechoic marks. Likewise, in case the detection of changes of tissue properties is done via the reflected radiofrequency signal, $t_{mark}$ is represented by the delay between the onset of the pulse and the detected change in the radiofrequency signal.

An example of a radiofrequency coupler which can be applied for the above mentioned purpose is the Werlatone 40 dB Dual Directional Coupler, Model C5571. For this application only the reverse power coupling port will be used.

Such a measurement of the occurrence of changes of tissue properties allows for a cost-efficient and easy way to either only detect the occurrence of changes of tissue properties or preferably to determine the time until hyperechoic marks occurs, i.e. the determination of $t_{mark}$.

The devices as can further comprise means for storage of a reference curve and means for comparing measured values with a reference curve.

A reference curve can be based on experience, on theoretical deduction, on statistical evolutions or a combination thereof. Typically, one reference curve per clinical application is stored. Preferably, the reference curve contains expectancy values for $t_{mark}$ and/or $t_{on}$ in combination with an electrical power of the HIFU transducer. The reference curve may be calculated for different target depth or may include a derating factor allowing taking target depth into account The device can comprise a display for displaying the time $t_{mark}$ to an operator. The display enables the operator to adjust the power and the pulse duration of the HIFU transducer to obtain an optimal treatment result.

The device can comprise means for determining a power $P_e$ for subsequent HIFU pulses based on $t_{mark}$. Preferably, the power $P_e$ for subsequent pulses is determined based on $t_{mark}$ by means of a reference curve as described above.

Means for determining the power $P_e$ for subsequent pulses allow for an automatic adjustment based on the previous measurement and hence allow for an optimal treatment result.

The device can comprise several detectors, preferably at least two detectors.

The use of several detectors eliminates the random error of one detection means. Hence, a measurement is more reliable and accurate. Preferably, different methods for detection of changes of tissue properties are used, e.g. one based on ultrasound imagery of the therapy beam and one based on the characteristic features of the reflected radiofrequency signal or passive cavitation detection. As a matter of course, even other methods and various combinations are applicable. This also eliminates method-immanent measuring errors. The values of $t_{mark}$ determined by the different methods are preferably used as a basis for a resulting $t_{mark}$-value that is used for the determination of the power $P_e$ and/or pulse duration $t_{on}$.

The device can comprise several means for time measurement and means for determining an average $t_{mark}$ or for determining a weighted average time from different $t_{mark}$ values.

The detector preferably provides an indication of occurrence of $t_{mark}$ as well as a confidence value of the accuracy of the detection. The confidence value is taken into account for determination of the weighted average in a manner basically known to the skilled person.

The determination of a weighted average $t_{mark}$ enhances the accuracy of the adjustment of the treatment power.

According to another aspect of the invention there is provided a method for controlling a therapeutic treatment device, preferably a device as described above. The method comprises a step of monitoring a HIFU treatment by a HIFU transducer of a target by means of measuring a time $t_{mark}$, wherein the time $t_{mark}$ is the time from the beginning of emission of a HIFU pulse to detection of changes of tissue properties or by measuring the frequency of appearance of changes of tissue properties $f_{mark}$. In this case $t_{mark}$ can be substituted by $f_{mark}$.

Based on $t_{mark}$ or $f_{mark}$ several types of decisions can be made by the operator of the device or automatically by the device itself in order to better regulate the treatment.

The regulation of the treatment can be conducted by changing the power $P_e$ or the pulse duration $t_{on}$. Furthermore, the time between pulses $t_{off}$ and/or the special position of the pulses can be adapted.

Since the time $t_{mark}$ is correlated to the intensity of the HIFU beam in the target zone, this method provides for a cost-efficient and easy control of a HIFU treatment.

The analytical derivation of $t_{mark}$ can be done by the model by Parker, K. J., *Effects of heat conduction and sample size on ultrasonic absorption measurements. J Acoust Soc Am*, 1985. 77(2): p. 719-25. The model expresses the temperature rise in the focus of a HIFU pulse by solving the bio-heat transfer equation. During the pulse the increase in temperature $\Delta T$ at time t is given by:

$$\Delta T = \frac{2*\alpha*I}{\rho_0*C_0} * \frac{a^2}{4*k_0} * \exp(-r^2/a^2) * \ln\left(1 + \frac{4*k_0}{a^2}*t\right) \quad (1)$$

Where:
r=distance from the beam axis,
I=in-situ intensity of the HIFU pulse which is roughly proportional to $P_e$
a=half width of the focus in tissue
$\kappa_0$=thermal conductivity of tissue,
$C_0$=thermal capacity of tissue
$\rho_0$=density of tissue,
Simplifying the notation gives:

$$\Delta T = I*B_0*t_0*\exp(-r^2/a^2)*\ln\left(1+\frac{t}{t_0}\right) \quad (2)$$

-continued $$t_0 = \frac{a^2}{4*k_0} \quad (3)$$

with:

Where $t_0$ represents the time required for heat to diffuse through the focus; and $$B_0 = \frac{2*\alpha}{\rho_0 * C_0}; \quad (4)$$

$B_0$ only depends on the tissue.

Equation 2 can be inverted to obtain the time t at which a certain temperature increase $\Delta T$ is obtained.

$$t = t_0 * \left[\exp\left(\frac{\Delta T}{I*t_0*B_0}\right) - 1\right] \quad (5)$$

$t_{mark}$ is the time when the boiling temperature $T_{boil}$ is reached and hyperechoic marks can be detected. In this case a tissue temperature of 37° C. before application of the pulse is assumed.

$$t_{Mark} = t_0 * \left[\exp\left(\frac{T_{Boil} - 37}{I*t_0*B_0}\right) - 1\right] \quad (6)$$

Hyperechoic marks can be detected by measuring the variation of a pattern of interference during HIFU pulse. The interference occurs between ultrasound waves from an imaging ultrasound transducer and an acoustic treatment transducer.

A measurement of the occurrence of hyperechoic marks by measuring the variation of a pattern of interference during a HIFU pulse does not interrupt the treatment and hence enhances the efficiency of the treatment. Furthermore, the measurement by another ultrasound transducer is cost-efficient.

According to another aspect of the invention, there is provided a method for controlling a therapeutic treatment device preferably as described above. The method comprises the step of determining changes of tissue properties by detecting characteristic features of a reflected radiofrequency (RF) signal by means of an radiofrequency (RF) coupler on a power line of the HIFU transducer.

Such a method is reliable and simple and does not require a supplemental transducer to achieve the goal of observing a HIFU pulse.

The changes of tissue properties can be detected by a acoustic imaging transducer, preferably a second acoustic imaging transducer, able to emit waves to provide an imaged representation of the target and of its environment.

The detection of changes of tissue properties by a second acoustic imaging transducer is cost-efficient and leads to reliable determination of $t_{mark}$.

The therapeutic treatment device can be initialized, wherein the initialization is directed to the values of pulse duration $t_{on}$ and/or pulse power $P_e$, whereby the initialization includes the steps of emitting at least one initial calibration HIFU pulse from an acoustic treatment transducer onto a target to be treated at an electrical power $P_1$. The time $t_{mark}$ between the beginning of emission of the initial calibration HIFU pulse and detection of changes of tissue properties can be measured and the electrical power $P_e$ for subsequent pulses can be determined in order to obtain a predefined intensity of HIFU at the target.

The initialization can further be based on a theoretical value of $P_1$ or a value based on experience or a combination thereof instead of or in addition to the initial calibration HIFU pulse. The electrical power $P_e$ is determined based on the known variables after initialization $P_1$ and $t_{mark}$. In simple cases this could be a linear transformation or a proportional integral derivative (PID). More generally a curve such as the one representing equation (6) may be used. Since the bio-heat transfer equation is a differential equation in most of the cases, the adaptation of $P_e$ can be based on predefined curves for the specific clinical application to get an accurate result.

The power $P_e$ of the HIFU pulse emitted from the acoustic treatment transducer can be adapted on the value of $t_{mark}$ measured for the previous pulse or based on the evolution of $t_{mark}$ over several previous pulses and consequent adjustment of the electrical power $P_e$ and/or the time $t_{on}$.

The adaption of the power $P_e$ based on one or more previous pulses enables the control of the treatment and hence leads to a safe and efficient treatment.

Furthermore, the power $P_e$ or $t_{on}$ of the HIFU-pulse emitted from the acoustic treatment transducer can be adapted based on the frequency of appearance of changes of tissue properties.

The adaption of the power $P_e$ or $t_{on}$ based on the frequency of appearance of changes of tissue properties also enables the control of the treatment and leads to a safe and efficient treatment.

The adjustment of the power based on $t_{mark}$ or on the evolution of $t_{mark}$ can be conducted while taking into account its inherent dispersion by applying techniques inspired by statistical process control or filtering.

The method can comprise the following steps:
  determining a time $T_{mark1}$ from the beginning of the emission of a HIFU pulse until hyperechoic marks are detected with a first method of detection hyperechoic marks,
  determining a second time $T_{mark2}$ with a second method different from the first,
  determining $t_{mark}$ on the basis of $T_{mark1}$ and $T_{mark2}$.

This approach leads to a more reliable determination of $t_{mark}$ since random errors are reduced.

The invention is described in the following by means of embodiments.

FIG. 1 Schematic view of a treatment device

Figure 2:
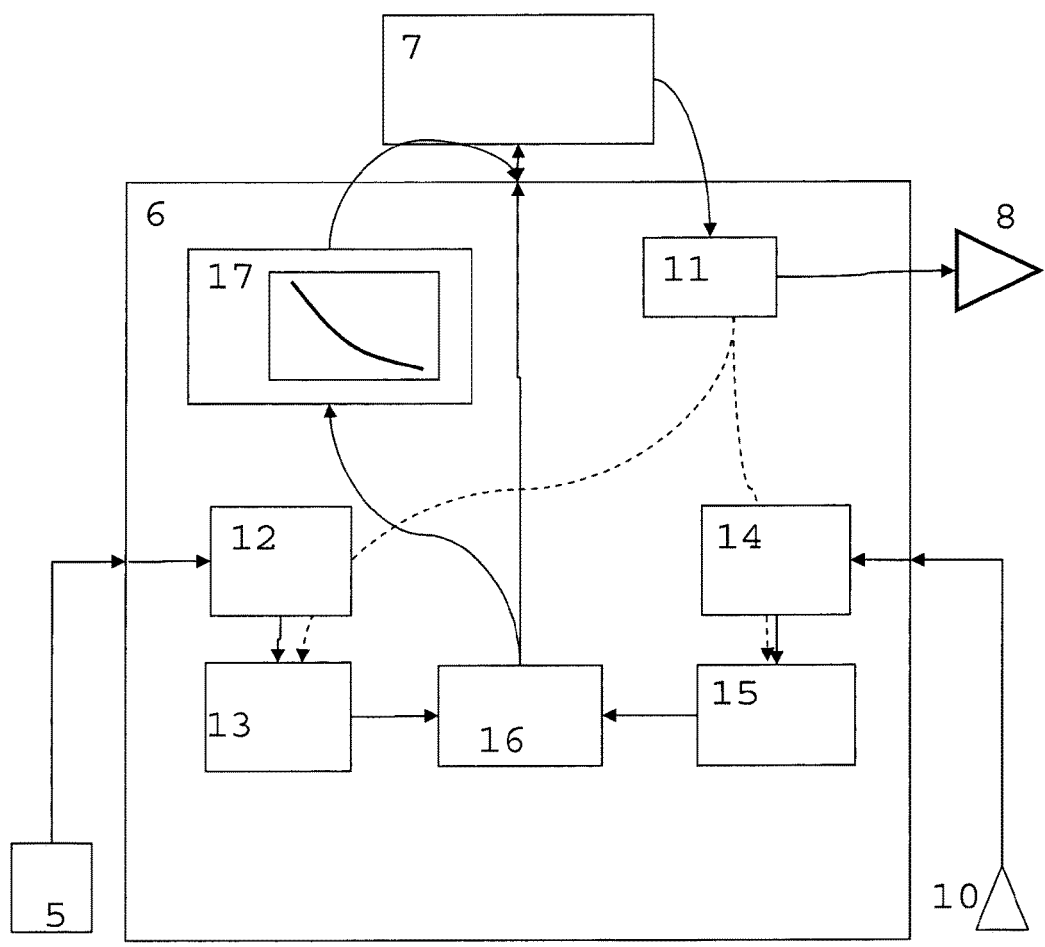
Figure 3:
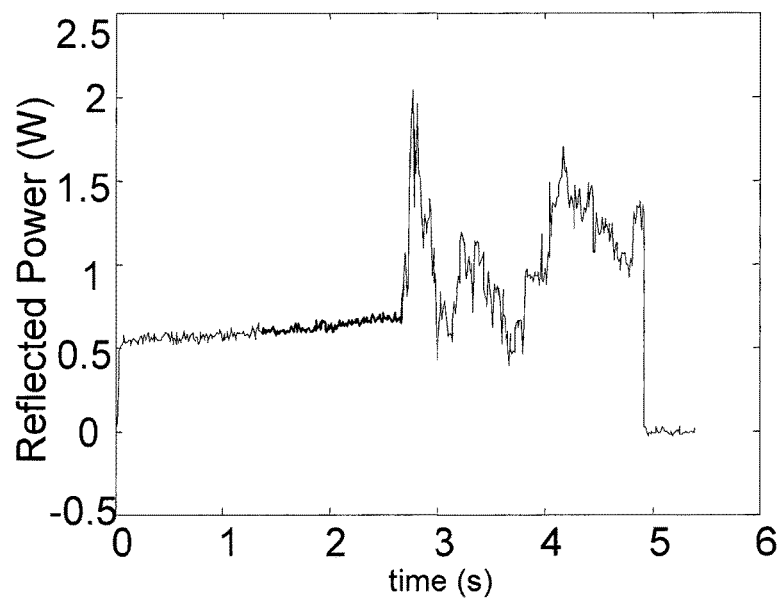
Figure 4:
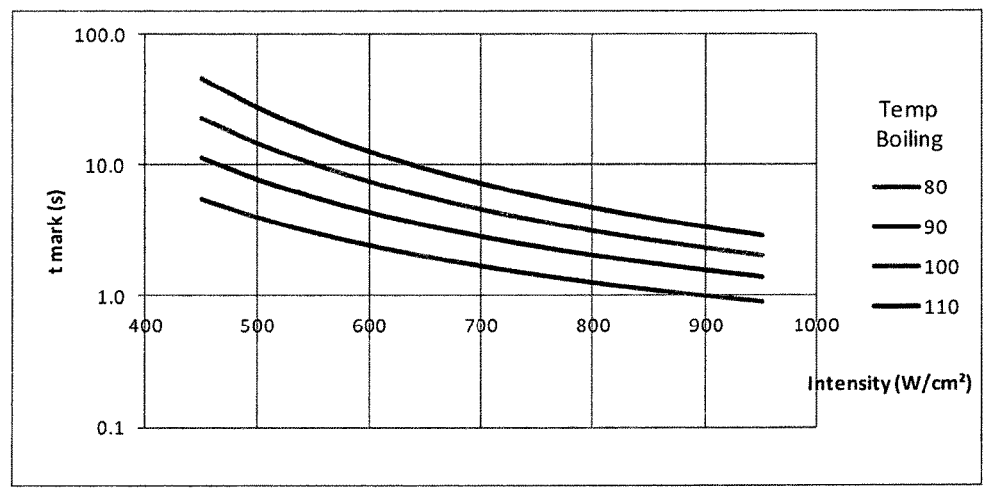
Figure 5:
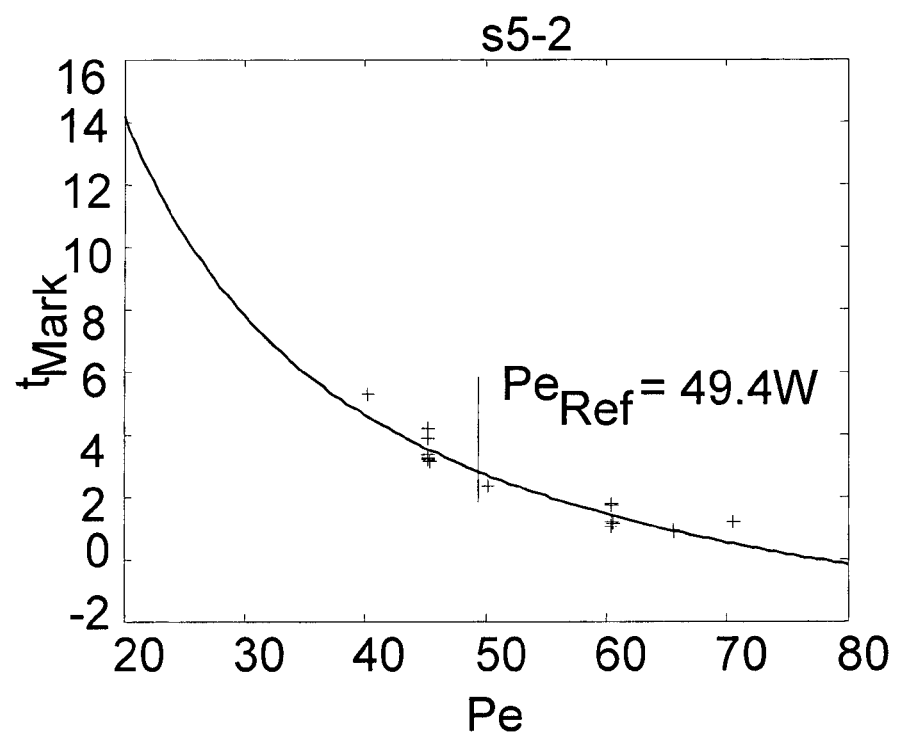
Figure 6:
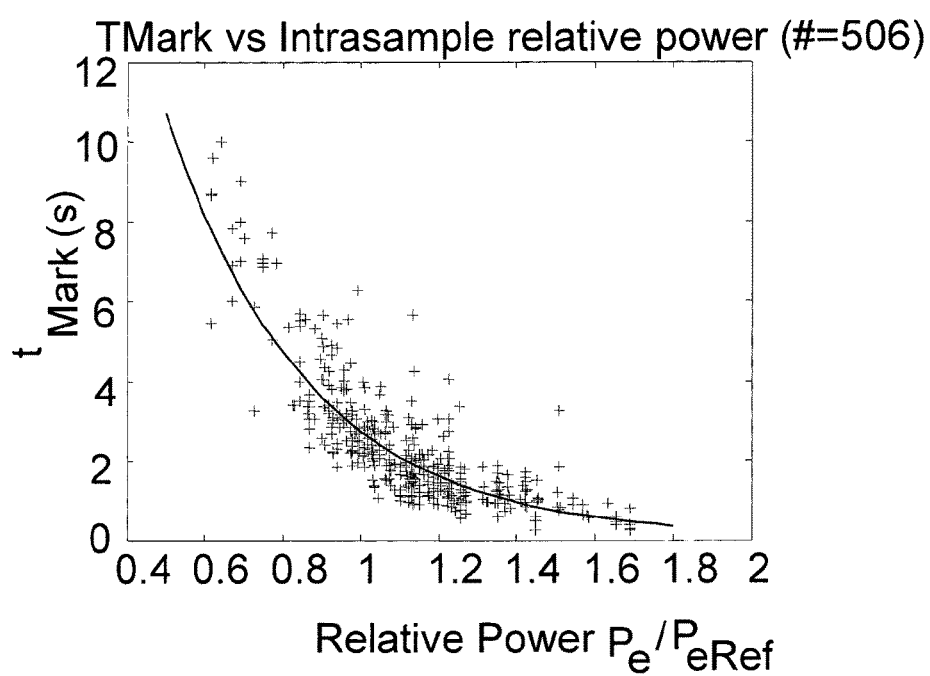
Figure 7:
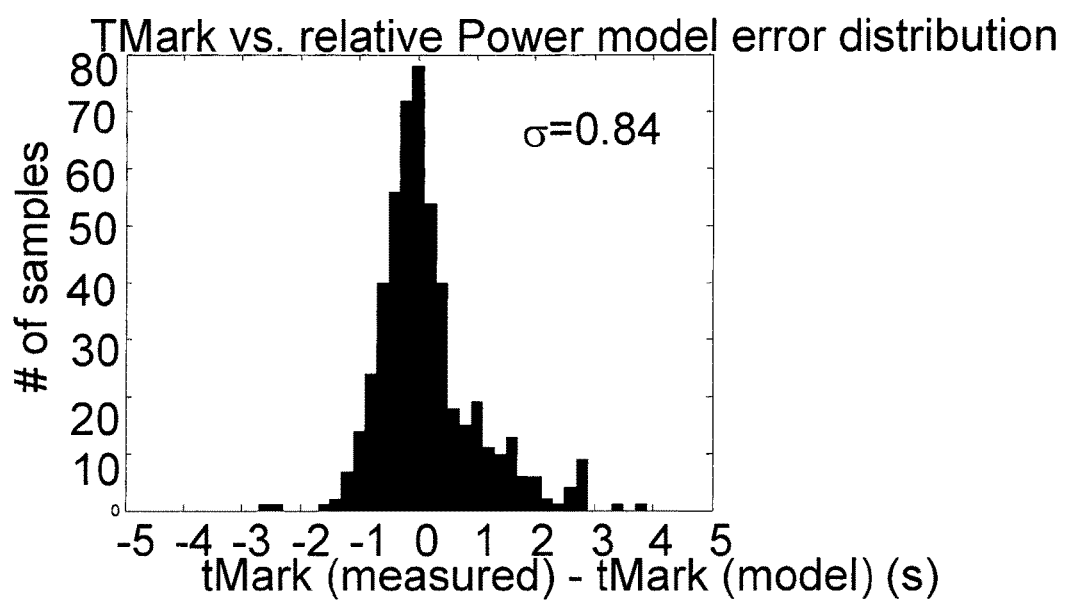
Figure 8:
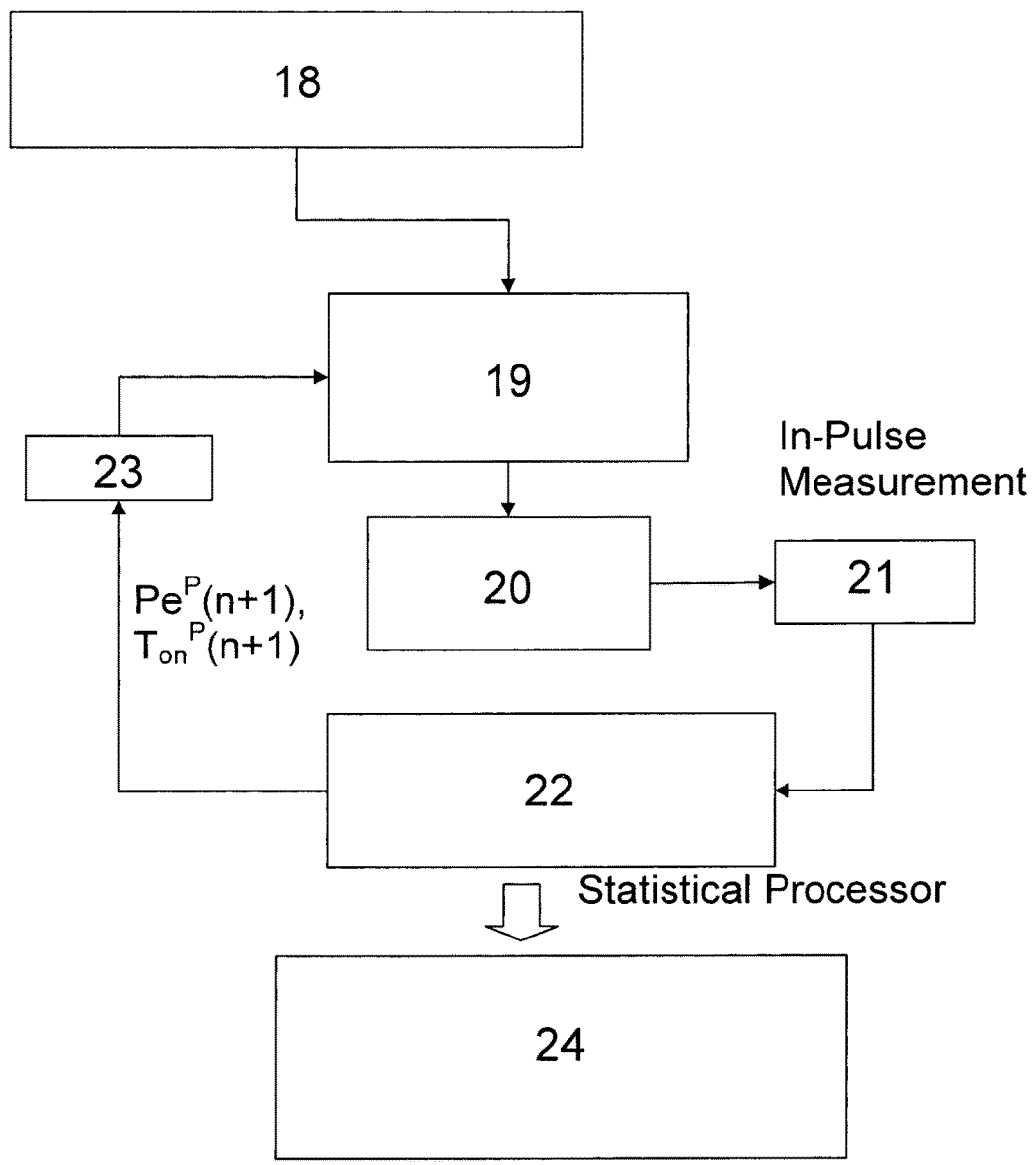
Figure 9:
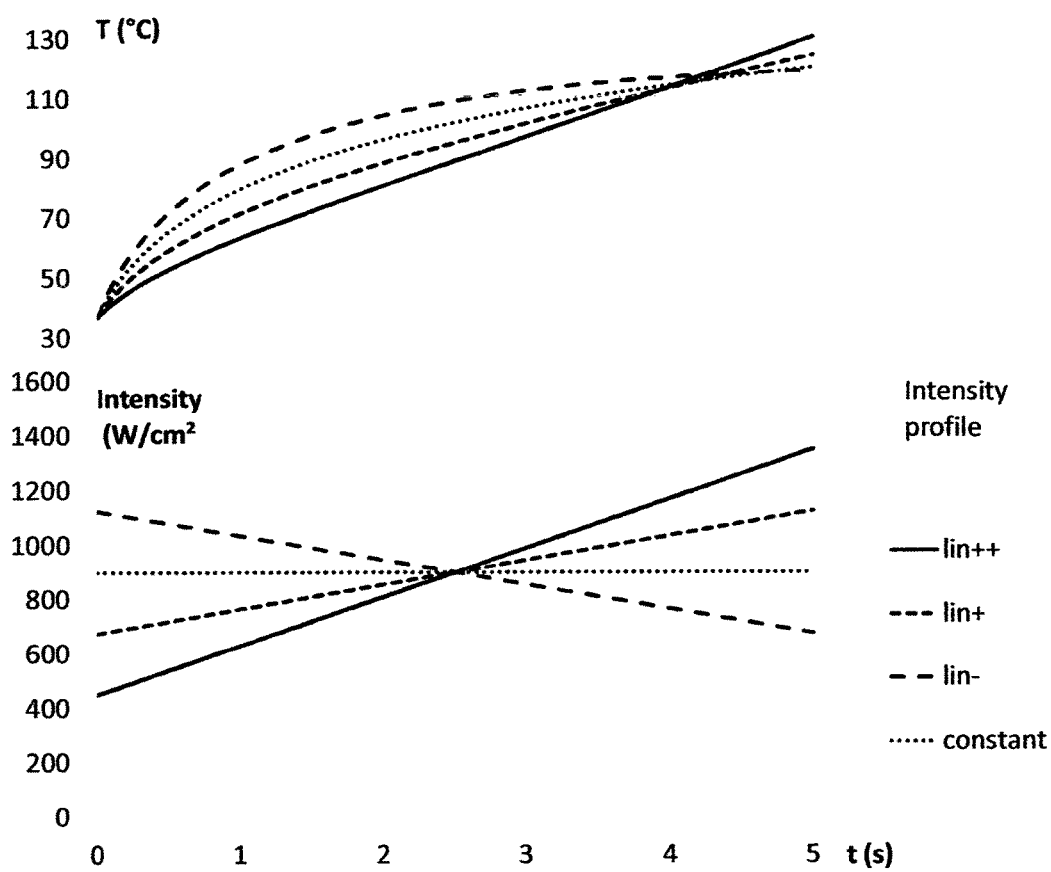

FIG. 2 Schematic view of a radiofrequency coupler for determination of the reflected HIFU signal FIG. 3 graphic view of an example of a reflected signal envelope FIG. 4 graphic view of calculated times to HEM over intensities for various boiling temperatures FIG. 5 graphic view of a determination of $P_{eref}$ in a given sample FIG. 6 graphic view of $t_{mark}$ over a standardized $P_e$ of a complete sample FIG. 7 graphic view of $t_{mark}$ error distribution FIG. 8 usage of the statistical model over the course of a treatment FIG. 9 temperature profiles and intensity profiles. The constant line, where the intensity is kept constant is shown for comparison.

FIG. 1 shows a schematic overview of a treatment device 1 according to the invention.

The device 1 is controlled by the user through a graphical user interface 7 (for instance a touchscreen). The processing unit 6 allows control of the interaction between the different subsystems.

An acoustic treatment transducer 2 emits high intensity acoustic waves (HIFU Beam) 2b onto a target 3. The HIFU waves are focused onto the target 3 within a target area. A radiofrequency generator 8 provides the necessary radiofrequency power for generation of the HIFU beam. This radiofrequency generator 8 is controlled both in terms of power and timing by the processing unit 6. An ultrasound imagery transducer 4 allows the observation of the target area and of the beam propagation, provided that its field of view 4b encompasses the HIFU beam focal point. An ultrasound scanner 5 generates an image stream that is fed to the processing unit 6.

The reflected power signal is tapped on the radiofrequency power line by a radiofrequency directional coupler 9, and then fed to the processing unit 6 through an Analog to Digital Conversion (ADC) unit 10. The processing unit 6 contains a circuit/algorithm to detect a change in the RF signal. A counter/timer measures the time between the onset of the pulse and the instant the RF signal changes.

FIG. 2 shows a preferred embodiment of the processing occurring in the processing unit 6. The processing unit 6 provides a common timebase 11 that will allow synchronization of HIFU emission by radiofrequency generator 8 with detection of HEM. This feature allows deriving $t_{Mark}$ from the knowledge of HIFU pulse timing and detection of HEM.

The ultrasound image stream coming from ultrasound scanner 5 is fed to image processor 12 where a technique such as the one described in WO 2010/020730 allows retrieving information on the presence of interference patterns. The output of this processor is fed to detector 13 which infers $T_{Mark}^{Image}$, along with detection quality information from the output of 13 and from the timing information provided by timebase 11.

The reflected radiofrequency signal provided by the analog to digital conversion unit 10 is processed by signal processor 14 in order to retrieve features such as its envelope and/or its spectral content. These features are then provided to HEM detector 15, along with timing information from timebase 11 to obtain $T_{Mark}^{RF}$ along with detection quality information.

Both $T_{Mark}^{Image}$ and $T_{Mark}^{RF}$ are then used by processor 16 to provide a best estimate of $T_{Mark}$ to the user through the graphic user interface 7.

As a complement, direct outputs from processors 12 & 14 may be directly provided to the user for supplemental information. An example of a reflected power signal is provided in FIG. 3. This example yields a $T_{mark}^{RF}$ of 2.67 s.

On the basis of this information, the user is able to adapt treatment parameters (electrical power and $t_{on}$) and provide these to the control timebase for the next HIFU pulse.

As a complement, $T_{Mark}$ information may be provided to a model and statistical processor 17, that will compute the best estimate of electrical power to use for the next pulse as described above.

An example for deciding on a value for $P_e$, a decision table can be used. The following table corresponds to a case were a treatment is carried out with the objective of having hyperechoic marks appearing at $t_{MarkG}$=3 s. For the sake of simplicity, we consider that the intrinsic variability of $t_{Mark}$, σ=1 s. For each HIFU pulse, we use the model $t_{Mark}$=A (eB.PeRef/Pe-1) as a reference. This allows to define—when a mark appears—a value for $P_{eRef}(n)$ as:

$$Pe_{Ref}(n) = \frac{P_e(n)}{B} \ln\left(\frac{t_{Mark}(n)}{A}\right)$$

$P_{eRef}(n)$ is interpreted as the necessary electrical power that would have been necessary in the conditions of HIFU pulse n to obtain $t_{Mark}$=$t_{MarkG}$.

In a typical implementation, the case where no marks appear during a pulse, an arbitrary value such as 1.5*$t_{On}$ instead of $t_{Mark}$ is used to obtain a value for $Pe_{Ref}(n)$. This provides a value for each pulse.

| Inputs | | Output |
|---|---|---|
| $t_{Mark}$ (n) | $t_{Mark}$ (n − 1) | Pe (n + 1) |
| $t_{mark}^G$ − σ < tM < $t_{mark}^G$ + σ | any | Pe (n) |
| $t_{mark}^G$ + σ < tM < $t_{mark}^G$ + 2σ | $t_{mark}^G$ + σ < tM < $t_{mark}^G$ + 2σ | ($Pe_{Ref}(n)$ + $Pe_{Ref}(n − 1)$)/2 |
| | otherwise | Pe (n) |
| $t_{mark}^G$ + 2σ < tM or no HEM | any | ($Pe_{Ref}(n)$ + $Pe_{Ref}(n − 1)$)/2 |
| $t_{mark}^G$ − 2σ < tM < $t_{mark}^G$ − σ | $t_{mark}^G$ − 2σ < tM < $t_{mark}^G$ − σ | ($Pe_{Ref}(n)$ + $Pe_{Ref}(n − 1)$)/2 |
| | otherwise | Pe (n) |
| tM < $t_{mark}^G$ − 2σ | any | ($Pe_{Ref}(n)$ + $Pe_{Ref}(n − 1)$)/2 |

This information is also provided to the user through graphic user interface 7.

FIG. 3 shows an example of a reflected signal envelope. This example yields a $t_{mark}$ of 2.67 s.

FIG. 4 shows the calculated time $t_{mark}$ to hyperechoic marks as a function of intensity for various boiling temperatures. This curve links in situ acoustical intensity with $T_{Mark}$, and thus allows an indirect estimation of the in situ tissue characteristics. As can be seen in FIG. 4 and this is confirmed by experience, $t_{mark}$ is sharply dependent upon the intensity. Therefore if the intensity is too low, no mark will appear ($t_{mark}$>$t_{ON}$). Even if the intensity is constant, the appearance of hyperechoic marks will depend much upon the local characteristics of the tissue (these are translated as "boiling temperature" in the model) and it will be difficult to regulate the power with efficiency because so many $t_{mark}$ would be missing during the course of the treatment.

FIG. 5 shows the measured values of $t_{mark}$ over the power of the HIFU-device 1 (see FIG. 1) for one given sample with homogeneous coupling conditions. On each sample, a total of 15 to 25 HIFU pulses were delivered. In order to assess repeatability of $T_{Mark}$ in homogeneous situations, the following analysis was carried out:

By hypothesis, acoustical conditions are considered to be identical in a given sample: Coupling and pre-focal attenuation are the same for the whole sample. For a given sample, retrieve all values of $T_{Mark}$ and corresponding electrical power $P_e$. Obtain for the considered sample an estimate of the electrical power value $P_e$ for which $t_{Mark}$ would have been equal to $t_{MarkRef}$ value. Provide the best fit for the data with a mathematic model, in this case: $t_{mark}=A(e^{B/Pe}-1)$ Define $P_{eRef}$ for the considered sample as the value for which the mathematical model intercepts $t_{MarkRef}$. Some samples are rejected at this stage because of the lack of differentiation in terms of power (typically all lesions have been created with the same electrical power). For each lesion, calculate a standardized power, which is defined as $P_e/P_{eRef}$. The process is repeated for each sample, allowing to define a full dataset of $t_{Mark}$ over standardized power. The measurement of these delays has been carried in various coupling conditions (skin, various attenuations, etc. . . . ). The dataset consist of 55 samples. The corresponding result is presented in FIG. 6.

The data presented in FIG. 6 allows determining a model for $t_{mark}$ vs. relative power as an exponential with form: $T_{Mark}^{est} = t_{mark} = A(e^{B \cdot PeRef/Pe} - 1)$. The numerical expression for a $t_{mark}$ reference of 2.8 s gives A=0.77 s and B=96.98

On the basis of this model, it is possible to control treatment power $P_e$. By providing an assessment for $P_{eRef}$. This is obtained through the following steps:
1. $T_{Mark}(1)$ is measured through a first pulse with a given electrical power $P_e(1)$. By inversion of the model $t_{mark} = A(e^{B \cdot PeRef/Pe} - 1)$, an initial value of $P_{eRef}$ is calculated.
2. Once PeRef is calculated, it is possible to compute the electrical power to apply in order to obtain a given expected value for $T_{Mark}$
3. The process is iterated over the successive pulses in order to improve the estimation of $P_{eRef}$ on the basis of all data pairs {Pe(n), $T_{Mark}(n)$}, including the cases where no hyperechoic marks have been detected.

In a typical implementation, these steps are carried out by Statistical processor 17 of FIG. 2.

FIG. 7 shows a residual error distribution of $T_{Mark}^{est}$ with the aforementioned model. Variance is less than 1 s, even though the data set includes a wide variety of coupling situations.

FIG. 8 shows the usage of the statistical model over the course of a treatment. In step 18 the value is set to be n=1. The initial, application based proposed values for $P_{eP}(n=1)$, $T_{onP}(n=1)$ are determined. In step 19 the operator decides on the values of $P_e(n)$, $T_{on}(n)$ for pulse number n. In step 20 the HIFU Pulse n at Pe(n) is applied. In step 21 $T_{Mark}(n)$ is measured during the application of the pulse. In step 22 new proposed value for next pulse are computed based on the measurement of $T_{Mark}(n)$ and the knowledge of $P_e(n)$. For the following pulse in step 23 n=n+1 the operator again decides as in step 19. Step 24 is the end of the treatment. The values $P_e(n)$, $T_{Mark}(n)$ are collected to further improve the statistical model described in FIG. 6.

In an attempt to always obtain hyperechoic marks during each pulse, it is proposed to expose the tissue to pulses with increasing power over time. For example the electrical power could start with 80 We and ramp up to 200 We over a $t_{on}=4$ s pulse duration. If a change in tissue properties is detected, the pulse would be aborted, thus impeding over exposure.

A mathematical derivation yields the temperature rise as a function of time in the form of a differential equation:

$$\frac{dT}{dt} = I(t) * B_0 * \exp(-r^2/a^2) / \exp\left(\frac{\Delta T(t)}{I(t) * B_0 * I_0}\right) \quad (6)$$

FIG. 9 shows examples of profiles of intensity vs. time. The process is carried out numerically. The figure shows examples of temperature profiles calculated with variable power. With profile "Lin−" the intensity is decreased linearly with time, yielding an essentially flat temperature after a 4 s warm-up period. This type of profile could be used if hyperechoic marks are detected at the beginning of the pulse (for example during the scanning phase of the treatment) and the operator wants to maintain an essentially constant temperature throughout the pulse.

With profile "Lin+" the intensity is increased linearly with time, yielding an essentially linear temperature rise with time, after a 2 s warm-up period. This type of profile would be best if no hyperechoic marks are detected during the previous pulses (for example at the beginning of the treatment). Profile "Lin++" is similar to "Lin+" but the intensity rises more sharply with time. The result is an almost linear increase of temperature during the pulse.

If the intensity profile is sharp (starts low ends high, Lin++ in the graph) then T(t) is quickly (almost) linear: this means that there is high probability that T will reach $T_{boil}$ during the pulse, meaning that hyperechoic marks will always be visible. This will help in regulating the power.

In general, the example treatment procedure comprises two phases: An initialization phase and a treatment monitoring phase.

The initialization phase comprises the steps of:

An initial calibration HIFU pulse at a given electrical power is emitted from the HIFU treatment transducer. The initial power chosen is based on the knowledge of the specific clinical indication and will make HEM appear within a time typically 1 to 2 seconds. $t_{mark}$ is measured by device 1 as shown in FIGS. 1 & 2. Afterwards, the electrical power to use in order to obtain a given value of $t_{mark}$ is chosen. This is done by the application of the theoretical model for $t_{mark}$ as described in FIGS. 4-6. The treatment is then conducted based on the calculated value of the power of the HIFU transducer.

Within the treatment monitoring the values for $t_{Mark}$ are measured for each pulse. During the monitoring phase the power can be adjusted based on the evolution of $t_{mark}$. Preferably, the inherent dispersion is taken into account, for example by statistical process control. This can be done by the following decisions:

If $t_{mark}$ is within 1σ of the goal value, keep current power $P_e$. If $T_{Mark}$ remains twice in a row in the 1-2σ range (on the same side), increase or decrease the power $P_e$ by 1 power 'step'. If $t_{Mark}$ is over 2σ range, the power $P_e$ is increase or decrease by 1 power 'step'. In a typical application a power 'step' can be defined as 20% of the current value of electrical power: this provides a logarithmic scale of power values that is well adapted to the proposed exponential model linking $T_{Mark}$ and $P_e$.

The invention claimed is:
1. A device for therapeutic treatment comprising:
an acoustic treatment transducer able to emit high intensity waves (HIFU) toward a target in order to treat the target, and the high intensity waves having a focal point, and
at least one detector for detecting a change of tissue properties caused by the high intensity waves in the target which defines an end point indicative of an occurrence of the change of tissue properties, wherein the change of tissue properties is an occurrence of hyperechoic marks, and wherein,
the device comprises at least one processor:
for time measurement configured to measure a variable duration ($t_{mark}$) from between a starting point at a beginning of the emission of a pulse of HIFU until said end point, and
configured to determine at least one of a power ($P_e$) or a pulse duration ($t_{on}$) for each subsequent pulse of HIFU to be emitted toward said target, and the determination by the at least one processor is based on said duration ($t_{mark}$) of a previous pulse of HIFU; and
during operation of the device, the device continuously determines the duration ($t_{mark}$) for determining at least one of the power ($P_e$) or the duration ($t_{on}$) for each subsequent pulse of HIFU, and at least one of the power

($P_e$) and the duration ($t_{on}$) of the emitted HIFU pulse emitted is adapted based upon a value of the duration ($t_{mark}$) measured for the previous pulse or based on an evolution of the duration ($t_{mark}$) for several previous pulses to achieve adjustment of at least one of the power ($P_e$) and the duration ($t_{on}$) for each subsequent pulse of HIFU emitted by the acoustic treatment transducer.

2. The device according to claim 1 wherein the detector is a radiofrequency coupler detecting changes in a reflected radiofrequency signal to an HIFU transducer.

3. The device according to claim 1, wherein the detector comprises a second acoustic imaging transducer able to provide an imaged representation of the target and of an environment of the target.

4. The device according to claim 3, wherein the focal point of the emitted high intensity waves is in an ultrasound imaging plane of the second acoustic imaging transducer.

5. The device according to claim 1, wherein the detector comprises a device for detection of a variation of pattern of interference during a HIFU-pulse.

6. The device according to claim 1, wherein the device comprises a server for storage of a reference curve and a processor for comparing measured values with the reference curve.

7. The device according to claim 1, wherein the device comprises a display for displaying the duration ($t_{mark}$) to an operator.

8. The device according to claim 1, wherein the device comprises at least two detectors.

9. The device according to claim 1, wherein the device comprises at least two processors for time measurement and a calculator for determining an average duration ($t_{mark}$) based on different values of duration ($t_{mark}$) from the at least two different time measurement processors.

10. A method for controlling a therapeutic treatment device, the method comprising:
a) monitoring a HIFU-treatment by a HIFU transducer of a target by a processor for measuring a variable duration ($t_{mark}$), wherein the duration ($t_{mark}$) is the time between a start point at a beginning of an emission of a HIFU-pulse until an end point, wherein the end point is defined by detection of hyperechoic marks caused by said HIFU-pulse, and changes of tissue properties are detected by an acoustic imaging transducer able to provide an imaged representation of the target and of an environment, and
b) determining at least one of an electrical power ($P_e$) or a pulse duration ($t_{on}$) of each subsequent HIFU-pulse, emitted from the HIFU transducer, with the processor, and said determination by the processor is based on a value of the duration ($t_{mark}$) measured for a previous pulse or based on evolution of the duration ($t_{mark}$) over several previous pulses and consequent adjustment of the electrical power ($P_e$) in order to compensate for variations in transmission of HIFU waves by intervening tissue, and
c) continuously determining, during operation of the device, the duration ($t_{mark}$) to determine at least one of the power ($P_e$) or the duration ($t_{on}$) for each subsequent pulse of the HIFU,
d) adapting at least one of the power ($P_e$) and the duration ($t_{on}$) of the emitted HIFU pulse based upon a value of the duration ($t_{mark}$) measured for the previous pulse or based on an evolution of the duration ($t_{mark}$) for several previous pulses to achieve adjustment of at least one of the power ($P_e$) and the duration ($t_{on}$) for each subsequent pulse of the HIFU emitted by the acoustic treatment transducer.

11. The method according to claim 10, wherein tissue changes are detected by determining characteristic features of a reflected radiofrequency (RF) signal by a radiofrequency directional coupler on a power line of the HIFU-transducer.

12. The method according to claim 10, wherein the therapeutic treatment device is initialized, and the initialization includes:
emitting at least one initial calibration HIFU-pulse from an acoustic treatment
transducer onto the target to be treated at an electrical power ($P_1$), and
measuring the duration ($t_{mark}$) between emission of the initial calibration HIFU-pulse with the processor and detection of changes of tissue properties, and
determining the electrical power ($P_e$) in order to obtain a predefined intensity of the HIFU at the target for subsequent pulses based on the duration ($t_{mark}$) measured for the previous pulse.

* * * * *